(12) United States Patent
Courtney et al.

(10) Patent No.: US 7,906,768 B2
(45) Date of Patent: Mar. 15, 2011

(54) IMAGING OF BIOLOGICAL SAMPLES

(75) Inventors: Patrick Courtney, Beaconsfield (GB);
Paul Orange, Beaconsfield (GB); Janet Park, Beaconsfield (GB); Claire Hooper, Beaconsfield (GB)

(73) Assignee: PerkinElmer Singapore Pte Ltd. (SG)

( * ) Notice: Subject to any disclaimer, the term of this patent is extended or adjusted under 35 U.S.C. 154(b) by 146 days.

(21) Appl. No.: 12/159,790

(22) PCT Filed: Jan. 19, 2007

(86) PCT No.: PCT/GB2007/000174
§ 371 (c)(1),
(2), (4) Date: Oct. 2, 2008

(87) PCT Pub. No.: WO2007/083138
PCT Pub. Date: Jul. 26, 2007

(65) Prior Publication Data
US 2009/0173892 A1    Jul. 9, 2009

(30) Foreign Application Priority Data
Jan. 20, 2006    (GB) ................... 0601183.7

(51) Int. Cl.
*G01J 1/58*    (2006.01)
(52) U.S. Cl. .................................. 250/484.4
(58) Field of Classification Search ......... 250/484.4, 250/459.1, 461.2; 435/6
See application file for complete search history.

(56) References Cited

U.S. PATENT DOCUMENTS

| | | | |
|---|---|---|---|
| 5,329,127 A | 7/1994 | Becker | |
| 5,504,337 A * | 4/1996 | Lakowicz et al. | 250/461.2 |
| 6,297,018 B1 | 10/2001 | French | |
| 2003/0117618 A1 * | 6/2003 | Itoh et al. | 356/317 |
| 2004/0072200 A1 | 4/2004 | Rigler | |
| 2004/0191792 A1 * | 9/2004 | Smith et al. | 435/6 |
| 2005/0158864 A1 | 7/2005 | Brant | |

FOREIGN PATENT DOCUMENTS
EP    0617286 A2    9/1994

OTHER PUBLICATIONS

Brockhinke, "Structural changes in the Ras protein revelaed by fluorescence spectroscopy", Phys. Chem. Chem. Phys., vol. 5, No. 16, Aug. 15, 2003, pp. 3498-3506.

Periasamy, "Fluorescence spectroscopy: New developments", Science Letters, vol. 26, No. 9 & 10, 2003, pp. 251-258.

* cited by examiner

*Primary Examiner* — David P Porta
*Assistant Examiner* — Marcus H Taningco
(74) *Attorney, Agent, or Firm* — Barnes & Thornburg LLP

(57) ABSTRACT

Methods and apparatus relating to the imaging of biological samples are provided. More particularly, they relate to the detection of light emanating from fluorescent species present in a sample in order to study the structure and dynamics of such a sample. Such a method of analysis comprises irradiating the sample with a pulse of excitation energy causing fluorescent species in the sample to fluoresce; detecting light emanating from the sample during a predetermined period of time after the pulse; generating and storing data recording at least the wavelength of the detected light against time; and analysing the data with reference to the respective lifetimes of the fluorescent species to detect the presence of the respective emissions from three or more different fluorescent species which emit light simultaneously during at least part of said predetermined period, which are indistinguishable from each other on the basis of their wavelength or lifetime alone.

9 Claims, 13 Drawing Sheets

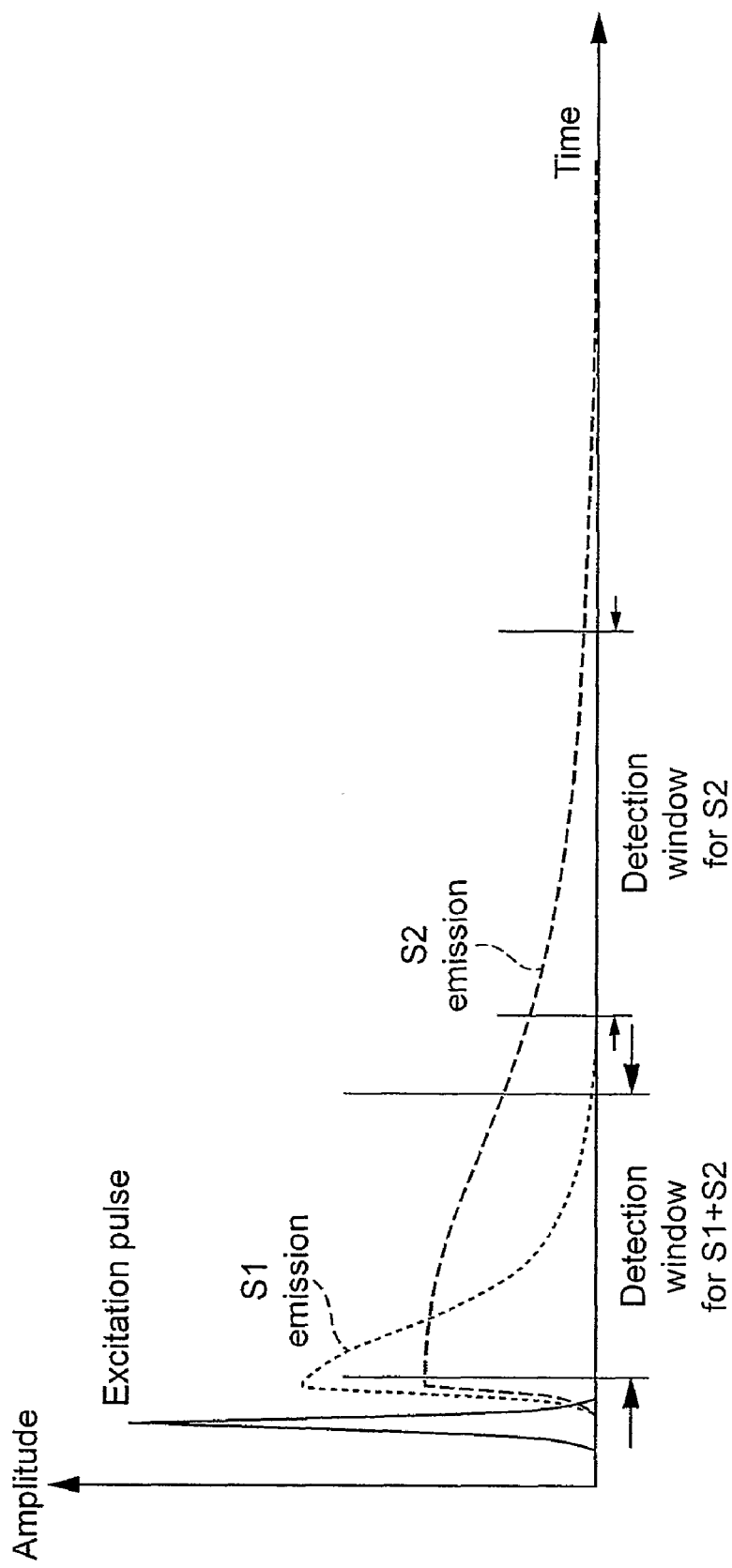

IMAGING OF BIOLOGICAL SAMPLES

FIELD OF THE INVENTION

The present invention relates to the imaging of biological samples and more particularly to the detection of light emanating from fluorescent species present in a sample in order to study the structure and dynamics of such a sample.

BACKGROUND TO THE INVENTION

Cells are highly complex entities and their study requires the collection of information on multiple interacting components and thus multiple parameters (multiplexing). The conventional approach is to use multiple fluorescent species introduced into (e.g. FITC) or synthesised within (e.g. GFP) or naturally occurring in (e.g. NADH) the sample, and matching detection channels (for different emission wavelengths) to collect such information, one channel per label. This approach is generally limited to about three or four (N=3 or 4) multiplexed fluorescent species due to the spectral emission overlap of the labels and the spectral discriminating ability of the detector under low light conditions. Alternatively, fluorescent species may be distinguished on the basis of their fluorescent lifetime. Again, this is limited to a modest number of detection channels at any one time (M=2 or 3). Conventionally these detection modalities are available in different instruments and the information obtained must be correlated between experiments. Furthermore, the measurements have typically been made in cuvettes, which may contain complex mixtures of several components.
Spectrally Resolved Fluorescence Fluorescent species (fluorophores) typically exhibit an excitation spectrum (in the form of a peak) within a shorter wavelength range, and an emission spectrum (in the form of a peak) with a longer wavelength range (FIG. 1a), whereby the excitation spectrum describes the probability of an incident photon exciting the species in a ground state according to its wavelength. After a short period, the excited species typically emits a photon to return to the ground state. The probability that the emitted photon has a particular wavelength is described by the emission spectrum.

The fluorescence process is inefficient and the emission light is much less intense than the excitation light employed, typically much less than 1%. In a practical embodiment, a particular species is typically excited by light from a source with light emitted across a particular excitation waveband. Of the emitted light, a particular emission or detection waveband may be selected for delivery to a detection subsystem (FIG. 1b). The excitation may be a narrow band source such as a laser, or a broader band source such as a lamp (e.g. Xenon or Mercury) from which a suitable waveband is selected. The emission waveband may be selected by the use of an optical filter.

Since there is typically an overlap between the excitation spectrum and the emission spectrum of the fluorescent species, this places practical constraints on the excitation waveband and emission or detection wavebands that may be employed. It is desirable to employ a broad emission or detection waveband, since this gives a greater probability that emitted light is detected, and the more sensitive the instrument may be to that species. Since the excitation light is typically much more intense than the emission light, it is usually necessary to ensure that the emission waveband of the light available to the detector does not include any part of the excitation waveband used which would otherwise overwhelm the detector or cause a spurious background signal in the absence of any fluorescent species. Maintaining a low background is particularly important when the fluorescent species of interest may be present in low concentrations. Therefore, extending the emission or detection waveband towards to shorter wavelengths in order to increase the detection efficiency requires the excitation waveband to be placed further towards the shorter wavelengths, and possible away from the excitation peak, resulting in poorer excitation efficiency. The design of a particular embodiment typically involves a careful tradeoff of selection of excitation waveband and emission or detection wavebands.

When a sample includes two or more fluorescent species, the situation becomes more complex, and there is a further trade off to be made. Either the individual fluorescent species must be interrogated sequentially in time one after another (temporal multiplexing), or the multiple excitation waveband and emission wavebands must be selected so as to avoid interference. There is likely to be a lost of sensitivity compared detection with a single fluorescent species, since the choice of wavebands width and location is more limited (FIG. 1c). In any case, the fluorescent species employed must be carefully selected, since fluorescent species which have excitation and emission spectra that are too similar may not be distinguishable. Furthermore some fluorescent species have significant secondary peaks in their excitation and emission spectra which causes interference in the detection of multiple species, limiting the available sensitivity and the dynamic range.

Fluorescence detection methods may be applied to samples in cuvettes or wells and are available in a number of commercial instruments marketed by PerkinElmer, Thermo Electron Varioskan and Tecan, for example. With appropriate selection of additional components, they may also be applied as an imaging modality thus creating an image of a sample such as a cell or tissue where each pixel is represented by a number that corresponds to the value measured for that point. Suitable fluorescent microscopes are available from suppliers such as Zeiss, Nikon, Olympus and Leica and suitable components from suppliers such as CRI.

Imaging instruments equipped with multiple spectrally sensitive detectors have been described (32 in the Zeiss 510 META, for example). However, for many fluorescent species with broad emission peaks, the number of photons captured per channel is statistically similar so that it is not possible to overcome the limitation of spectral overlap and sensitivity [Neher 2004]. Typically, an instrument is limited measuring up to 3 fluorescent species when using the visible waveband (400 nm to 700 nm) and 4 fluorescent species if this is extended into the ultraviolet and infrared (250 nm to 1100 nm).

One application area of particular importance in the study of biological systems including research and drug development is a system known of FRET (Fluorescence Resonance Energy Transfer) [Berney 2003]. In this technique a species of interest is labelled with one fluorescent label (the donor) while a second species believed to interact with the first species is labelled with a further fluorescent label (the acceptor) carefully selected so that the emission spectrum of the donor provide a spectral overlap with the excitation spectrum of the acceptor. If the two species of interest come into close proximity (and other factors such as dipole orientation are favourable) then energy may be transferred from an excited donor to the acceptor which can then emit photons. Measuring the change in emission of both the donor and acceptor may then be used to determine the existence or otherwise of FRET and thus if the two species of interest are in close proximity and thus likely to interact. The method is particularly powerful when used in conjunction with biosensor probes where a domain sensitive to a particular species to be sensed is associated with two fluorophores, one acting as a donor and the other as an acceptor, arranged such that the presence of the species to be sensed modifies the geometry of the biosensors such that the configuration of the two fluorophores is altered and FRET is either enhanced or suppressed. Such biosensors sensitive to a number of cellular signalling species have been described, allowing pathways to be studied [Schultz 2005].

However the FRET technique suffers from a number of problems, including difficulty in making reliable measurement using spectral means due to crosstalk in both the excitation and the measurement channels, though these can sometimes be dealt with using adequate controls [Berney 2003]. The substantial spectral bandwidth taken up by the donor and acceptor excitation and emission peaks precludes running more than one FRET system within a given sample.

When the fluorescent species has a well defined excitation and emission spectra, it is possible to achieve a simplification of the situation and to obtain some multiplexing capability. For instance, quantum dots are well known for having a common excitation spectrum and very narrow emission peaks. Thus a single excitation wavelength can be used with several narrow band emission filters to detect several species simultaneously.

Time Resolved Fluorescence

An alternative approach to detecting and distinguishing fluorescent species is to modulate the excitation energy at high speed and to examine the resulting modulation in the emission energy. Many fluorescent species exhibit a characteristic decay (ranging from a few milliseconds to less than a nanosecond) between excitation and emission which is described as the lifetime (time to fall to 1/e of the original intensity). This parameter may be used to distinguish the species.

In FIG. 2 an excitation pulse stimulates species S1 and S2 with characteristic lifetimes T1 and T2, when T1 is much shorter than T2. Typically, this function may be carried out by pulsing the excitation source and timing the arrival of the emitted photons (time correlated single photon counting or TCSPC), measuring the light collected in a given time window after the excitation pulse (or time resolved fluorescence lifetime) or by measuring the phase shift between a frequency modulated source and the detection signal (frequency-domain method). By varying the time window and applying the appropriate corrections, fluorescent species may be distinguished. See [Munster 2005] for a recent review.

Some molecules have quite long lifetimes, with rare earth (Lanthanides) compounds and others (e.g. Ruthenium) exhibiting lifetimes in the range of up to 1000 microseconds and have been used to develop a range of assay methodologies useful in life science research. These are characterised by higher sensitivity and larger dynamic range than those based solely upon spectral discrimination due to the ability of the time resolved property which removed scatter and auto-fluorescence, resulting in better selectivity and contrast.

Many small molecules have lifetimes in the nanosecond range [ISS website]. For example the PURETIME range of molecules have lifetimes in the range 2 ns to 300 ns. Some biological tissues and cellular samples exhibit fluorescence when excited with short wavelength light (500 nm and shorter) due to intrinsic species such as FAD and NADH (auto-fluorescence). These species typically exhibit broadband emission with a short lifetime. This may be used as a source of contrast without additional labelling species, or may interfere with the observation of fluorescent species of interest.

Lifetime detection technologies and applications based on rare earth (Lanthanides) are commonly available as time resolved fluorescence (TRF) and nanosecond lifetime. A number of commercial instruments are available for reading from cuvettes or wells such as PerkinElmer EnVision, Thermo Electron Varioskan, Tecan Ultra, which employ flash lamps or pulsed diode sources. Suitable software converts the collected delay curves into lifetime estimates. Existing systems must be configured for a particular range of lifetime species and cannot deal with more than 2-3 species.

With appropriate selection of additional components, fluorescence lifetime measurement may also be applied as an imaging modality thus creating an image of a sample such as a cell or tissue where each pixel is represented by a number that corresponds to the value measured for that point. A number of such microscopes have been developed, including commercial multi-photon microscopes; customised frequency-domain systems using gated intensifier or multi-channel plate (MCP) with a CCD cameras; and those upgraded with TCSPC systems from suppliers such as Becker and Hickl which again perform the necessary post-processing to compute the lifetime estimates [Munster 2005]. However these systems tend to be very slow, taking many minutes to collect a single image making it hard to monitor kinetic processes.

FRET is a popular application for fluorescence lifetime measurement systems, since the fluorescence lifetime of donor is reduced when in the presence of a suitable acceptor (FIG. 3a). Measuring a change in donor lifetime is often less susceptible to artifacts than the spectral FRET method described earlier. Recently it has been proposed that the use of a 'dark' acceptor (one which has a non-radiative decay path and so does not emit and light) [Ganesan 2006] would result in a cleaner system where only the donor emission is observed (FIG. 3b) thus reducing the spectral bandwidth required.

Multiplexing

Existing approaches to discrimination between fluorescent species generally use wavelength only, as shown in FIG. 4a; or lifetime only, as shown in FIG. 4b. In FIG. 4a the two species A and B have a similar lifetime but different emission spectra, so a histogram in the photons in the spectral axis will show two peaks, but only one lifetime; On the other hand in FIG. 4b, A and C have a similar emission spectra but exhibit two distinct lifetimes, so the histogram shown two peaks in the lifetime but only one peak on the wavelength axis.

Limited time and spectrally resolved multiplexing has been described in [Vikström 2004] where two lanthanide (Europium excited at 340 nm, emitting at 615 nm with a characteristic lifetime of 730 us; and Samarium also excited at 340 nm, emitting at 643 nm with a characteristic lifetime 50 us) and one prompt fluorescence label (SYTO24 excited at 485 nm, emitting at 535 nm). However full multiplexing is not described, beyond detecting one species in wavelength, and two in lifetime. This is illustrated in FIG. 4c where F is the small molecule with nanosecond lifetime and 535 nm emission, while D and E are the long lifetime labels (730 us and 50 us both at 615-640 nm). As can be seen, even though there is the potential to discriminate labels with characteristic emission spectra or lifetime alone, the lifetime in the 535 nm channel is not measured.

In a further report [Vikström 2004b] describes an approach to assay 4 readouts: cell stress (using an absorbent dye), cell proliferation (using a Samarium-based label), DNA fragmentation (using a Europium-based label), and cell number (using a fluorescence dye) using a combination of absorbent, time-resolved fluorescence and fluorescence readout modes. The cited advantage is to be able to make all the necessary readings from the same well, thus saving materials and effort in comparison to traditional radioactive readouts. However the readouts are not made at the same time, in particular, the cells are fixed and labelled with antibodies before making the time-resolved fluorescence and fluorescence readout. The approach also uses a well plate reader (the EnVision system from PerkinElmer) with a point (PMT) detector to make the measurements and so does not use any imaging; and does not produce a time course of readings.

In [Hanley 2002] a combined spectral-lifetime microscope is described, this time based on a frequency-domain system with an MCP/CCD detector and a spatial light modulator (SLM) coding system to allow measurements to be made of both spectrum (50 bands across the range 430 nm to 750 nm) and lifetime and reconstructed using a Hadamard transform. The data presented is as shown in FIG. 4d where two populations A and B exhibit different lifetimes across the same emission range; and FIG. 4e with two populations A and B which exhibit variable lifetime according the emission waveband. See also [Hanley 2001].

A further approach to multiplex has been the use of biosensors which are sensitive to more than one biochemical species by changes in the excitation-emission spectrum with the presence of metal ions [Komatsu 2005] or kinases/phospholipases [Schultz 2005]. However these have the drawback that their intensity is both a measure of concentration of the biosensor and also of the species to which it is sensitive, thus confounding the two. Other controls must be put in place if absolute estimates are to be obtained.

SUMMARY OF THE INVENTION

The present invention provides a method of analysing a biological sample comprising:
(a) providing a biological sample including a plurality of fluorescent species;
(b) irradiating the sample with a pulse of excitation energy causing fluorescent species in the sample to fluoresce;
(c) detecting light emanating from the sample during a predetermined period of time after the pulse;
(d) generating and storing data recording at least the wavelength of the detected light against time; and
(e) analysing the data with reference to the respective lifetimes of the fluorescent species to detect the presence of the respective emissions from three or more different fluorescent species which emit light simultaneously during at least part of said predetermined period, which are indistinguishable from each other on the basis of their wavelength or lifetime alone.

The present method facilitates acquisition of a greater number of measures from a sample containing a number of fluorescent species, enabling a greater insight to be obtained into the structure and dynamics of the sample. Each time a sample is radiated with excitation energy, this may risk alteration and/or damage to the sample and therefore there is a need to maximise the amount of data and information that can be extracted from each excitation.

The current invention proposes the use of both wavelength and lifetime measurements techniques in combination. The concept is that if it is possible to discriminate between N species by wavelength measurements, and between M species by lifetime measurements, then it is possible to discriminate between a total of M×N species by careful parameterisation of the excitation and detection subsystems. We term this full or true multiplexing. In the system represented in FIG. 5 by way of example, through careful selection of fluorophores, it is possible to discriminate between the four species A B C and D by carrying out wavelength measurement and lifetime measurement and performing the necessary algebra. In this case, it increases the number of possible samples from typically max(M,N) and at best M+N−1, to M×N. If M=2 and N=3 (relatively modest numbers with technology today) then this represents an improvement from 3 or (2+3−1=)4 species to (2×3=)6 species. The advantages are faster acquisition, allowing faster processes to be studied, as well as less photo-bleaching. In this way, both the spectral and the lifetime characteristics of the labels can be exploited, greatly increasing the flexibility afforded to experiment developers.

In a preferred embodiment, the detection step (c) comprises detecting the intensity distribution of the light emanating from the sample across a range of wavelengths over said predetermined period of time, and detecting the combined intensity of the light emanating from the sample over said predetermined period of time. Signals generated by these detection procedures are then stored as data for analysis. For example, algebraic techniques may be used to deduce the presence of the respective emissions from three or more different fluorescent species in the sample from the collected data. Given knowledge of the fluorescent species present in a sample, simultaneous equations relating the detected intensities to the emissions of individual species can be developed and then solved using the collected data.

A sample may be irradiated by scanning a range of excitation energies. Also, the sample may be irradiated by a plurality of pulses of excitation energy of the same or a range of respective excitation energies.

In a further implementation, data related to the polarisation of light emanating from the sample may be stored and analysed. Extending the detection of light to other parameters, such as excitation wavelength and polarisation, permits even greater multiplexing, and therefore differentiation between an even greater number of fluorescent species.

Preferably, the spatial distribution of the light emanating from the sample is detected and recorded.

Light may be detected at a predetermined series of intervals during the predetermined period of time, or continuously during the predetermined period of time.

The present invention further provides apparatus for analysing a biological sample including a plurality of fluorescent species, the apparatus including processing means for analysing data recording light emanating from a sample during a predetermined period of time to detect the presence of the respective emissions from three or more different fluorescent species which emit light simultaneously during at least part of said predetermined period, which emissions are otherwise indistinguishable from each other on the basis of their wavelength or lifetime alone.

The apparatus may include light detection means selected from the following: at least one PMT, a spatially sensitive detector, an imaging detector, a spatially partitioned imaging detector, and an array of wavelength sensitive detectors.

According to a further aspect of the invention, an excitation light source may be employed which may be configured to emit a predetermined sequence of pulses. Preselection of the duration, waveband and/or intensity of all pulses, or each pulse individually, and/or the length of the interval between pulses may be facilitated.

Benefits provided by embodiments of the present invention include access to more relevant and more specific information about cellular systems by multiplexing multiple fluorescent species. In particular:

To separate similar fluorescent species. Fluorescent species with similar chemical structures will have similar chemical properties but similar fluorescence excitation/emission properties. It may be possible to discriminate them on the basis of lifetime without the need for additional controls, since these controls are provided by the internal measurements.

Background removal. Free fluorescent species which would otherwise create a strongly interfering background signal, may be distinguished from bound fluorescent species. This will be of utility in avoiding wash steps, permitting liquid phase assays, as well as permitting higher speed lifetime imaging, providing access to information about live cell behaviour, kinetics, modulation of cell activity and toxicological responses.

Multiplexing allows functional information be incorporated, including cell viability (alive/dead) as well as examination of heterogenous cell types (spatial imaging).

The lifetime and spectral properties of the fluorescent species will vary with the micro-environment of the species. Examining the variation with multiple measurements will provide access to information about the presence of multiple fluorescent species as well as the micro-environment of the species.

The parameters obtained may be employed in a screening system during drug development to determine assay endpoints, and in toxicity testing. Recent developments have led to high content screening systems where multiple parameters may be determined from multiple measures extracted from spatial and/or temporal analysis of images sets (translocation, etc) following stimulation. This approach could also be applied to the measures extracted using the approach described here.

BRIEF DESCRIPTION OF THE DRAWINGS

Embodiments of the invention will now be described by way of example and with reference to the accompanying schematic diagrams wherein:

FIG. 2 is a plot of amplitude against time illustrating fluorescence lifetime according to the prior art;

DETAILED DESCRIPTION

Figure 1A:
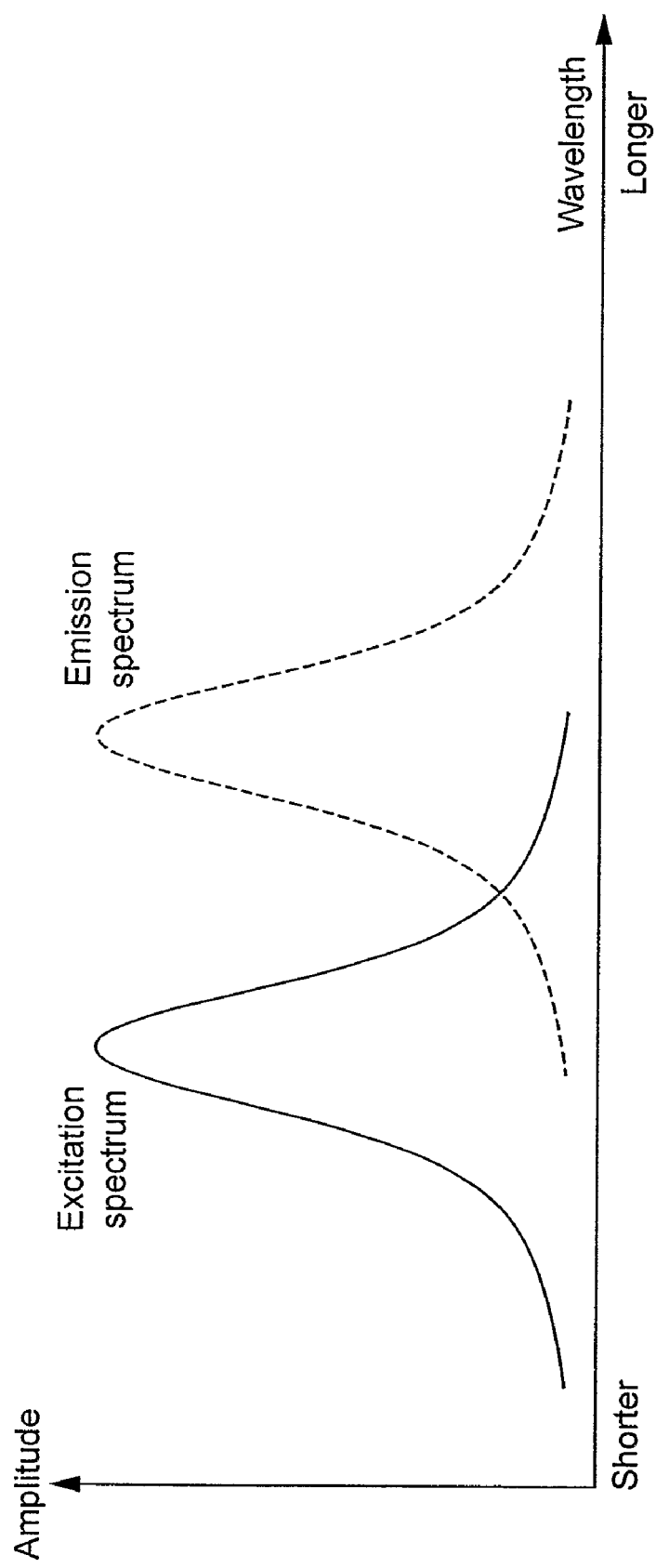
FIGS. 1a to 1c are plots of amplitude against wavelength illustrating prior art fluorescence detection techniques.
Figure 1B:
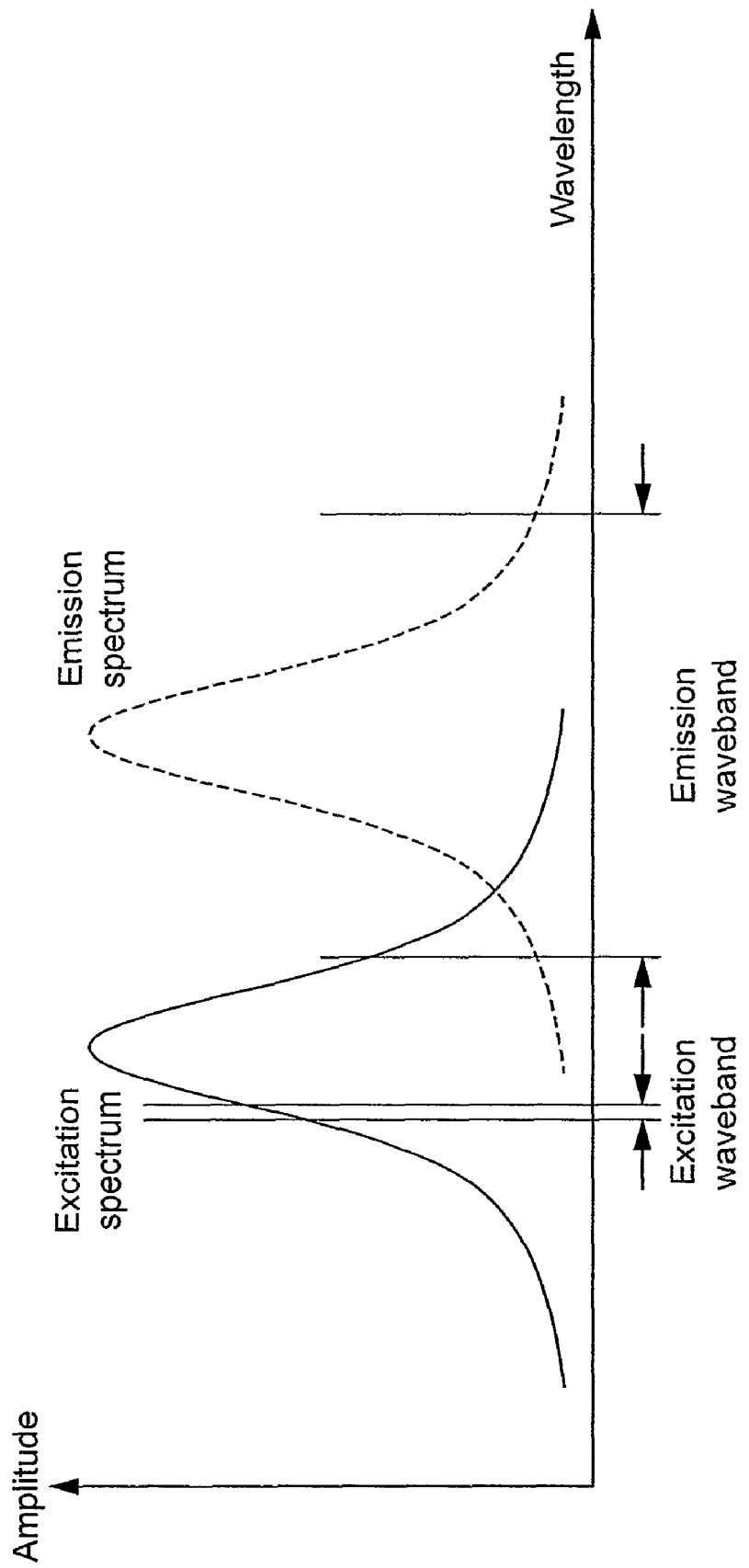
Figure 1C:
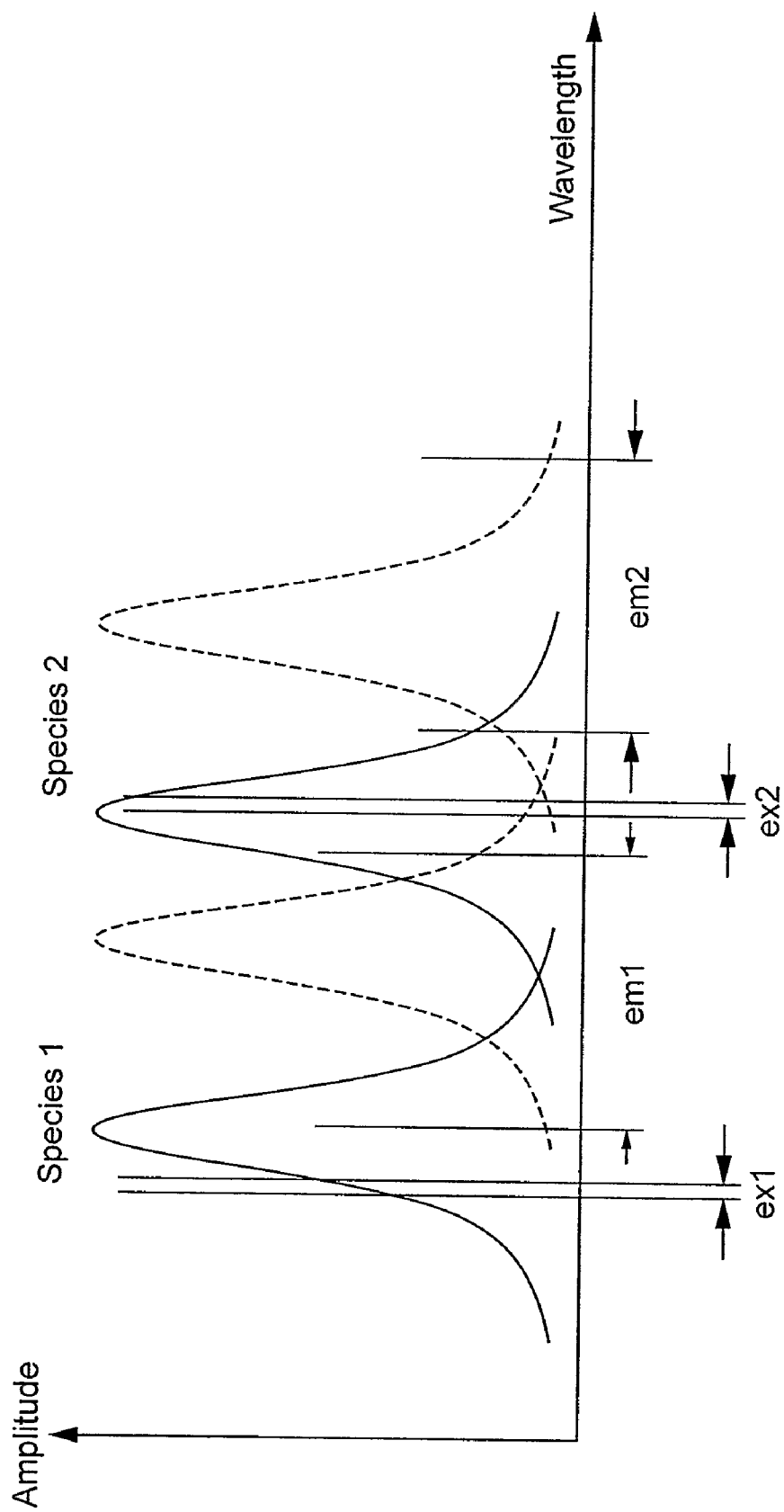
Figure 3A:
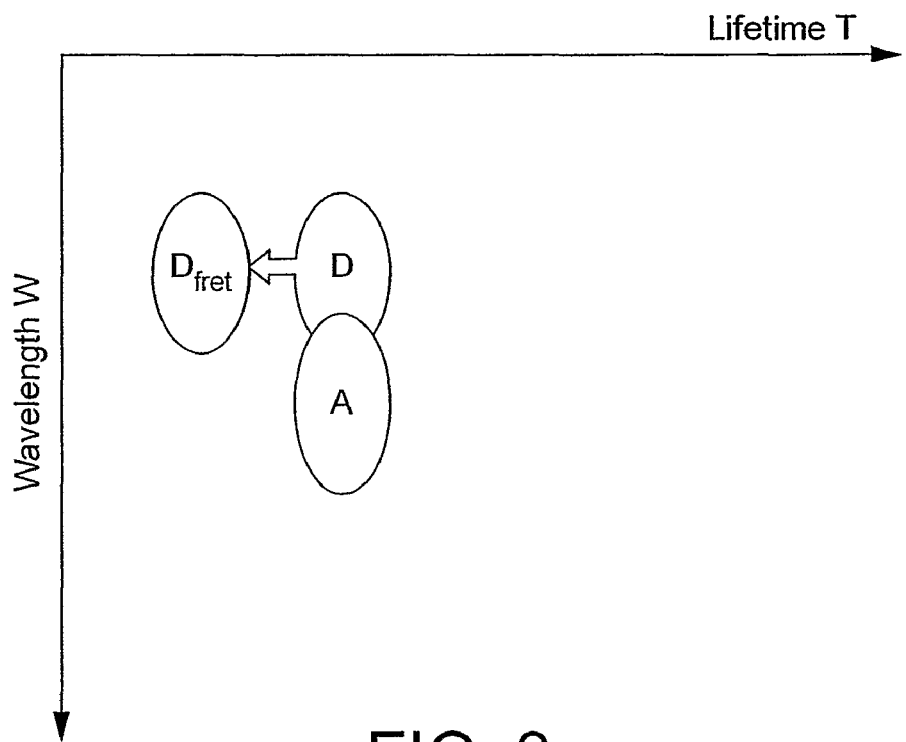
FIGS. 3a and 3b are plots of lifetime against wavelength illustrating known FRET techniques.
Figure 3B:
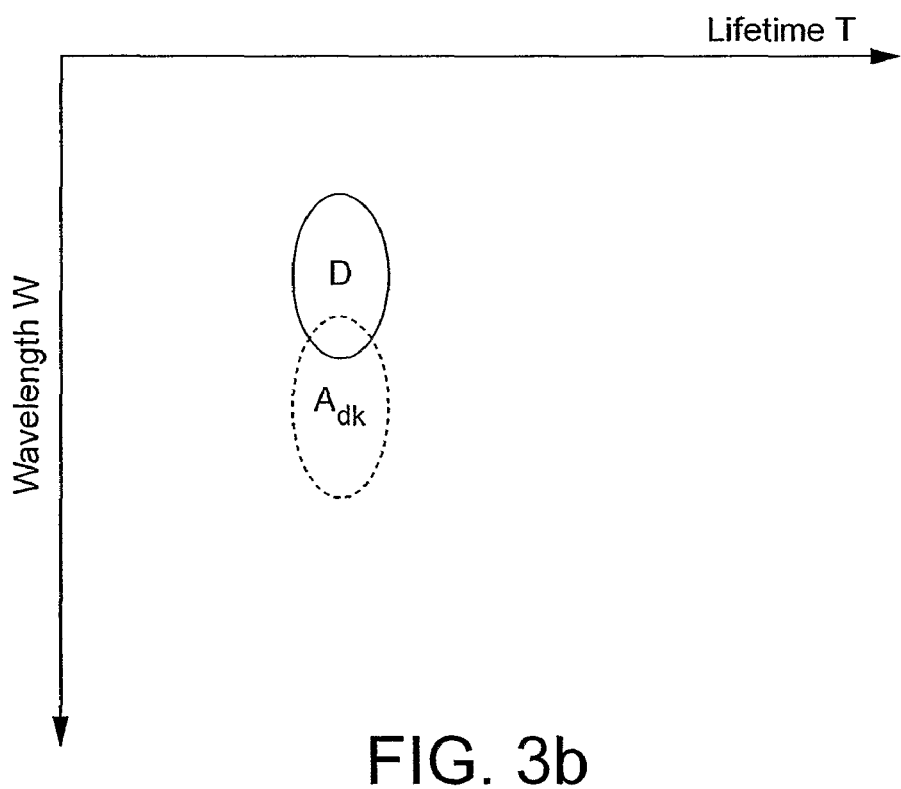
Figure 4A:
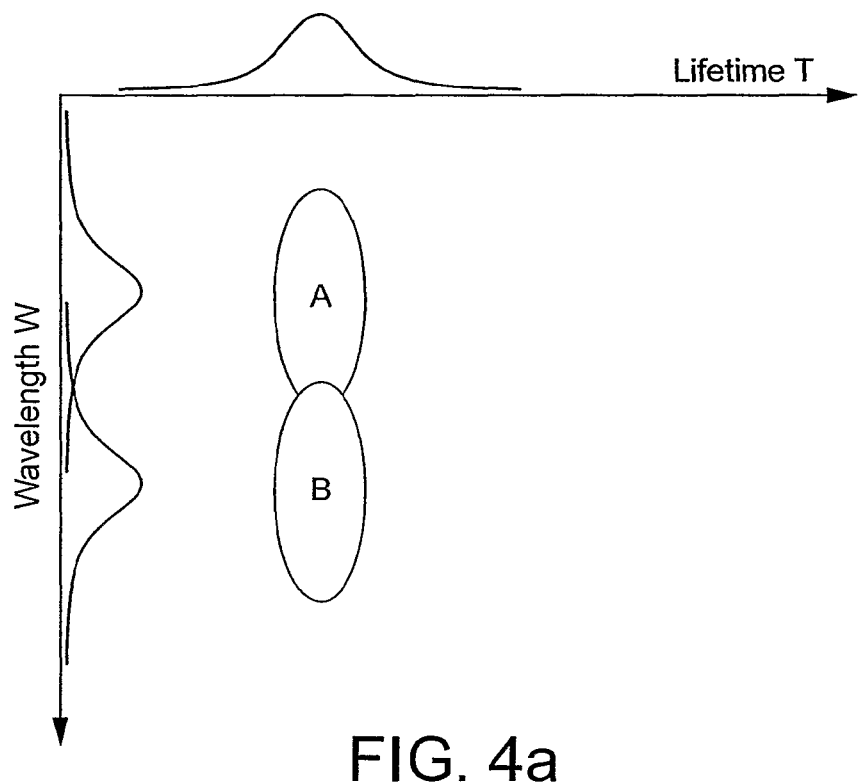
FIGS. 4a to 4e are plots of lifetime against wavelength illustrating discrimination between fluorescent species according to the prior art.
Figure 4B:
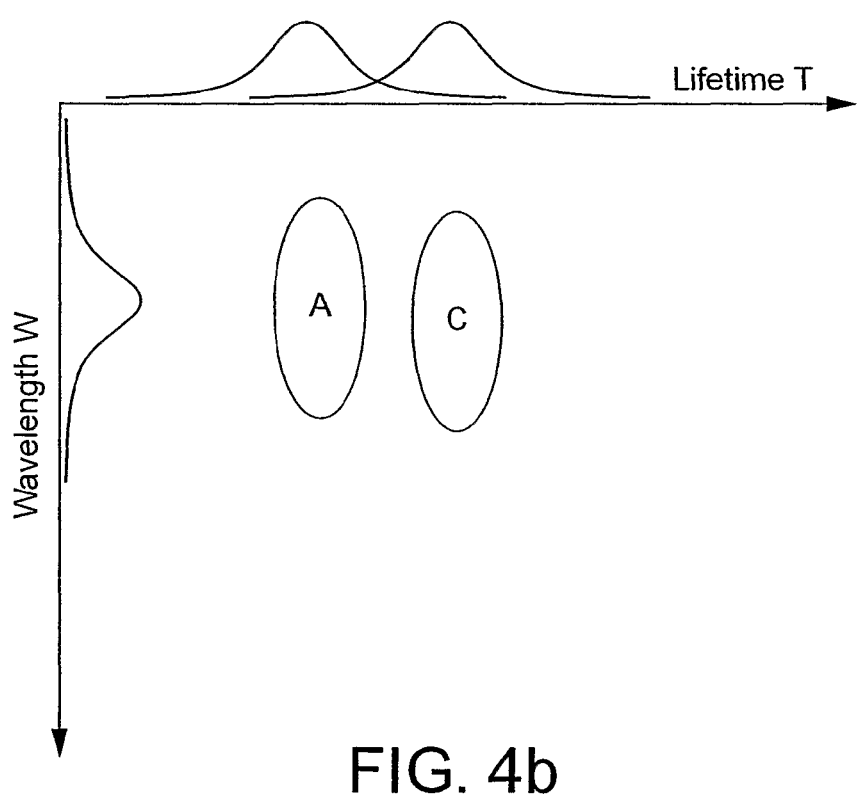
Figure 4C:
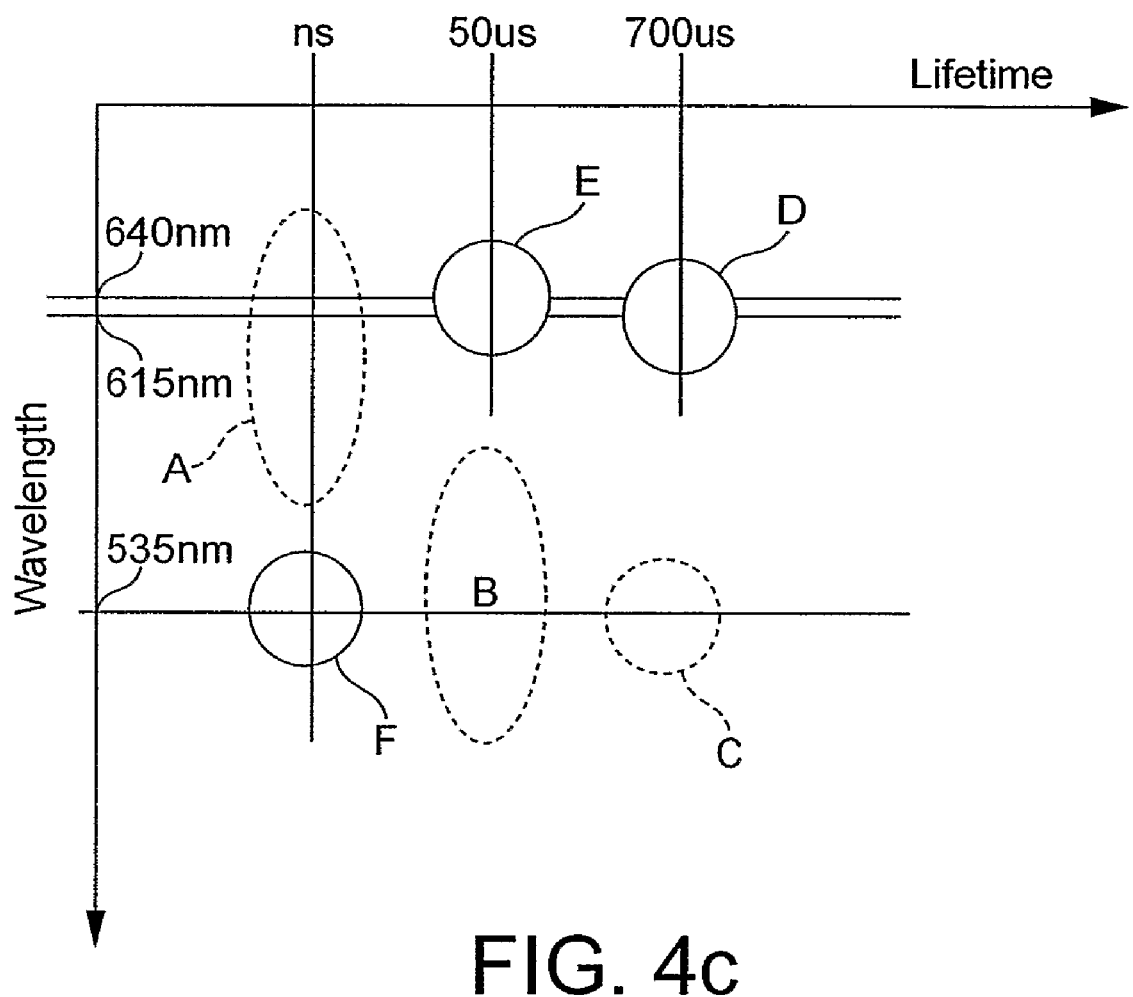
Figure 4D:
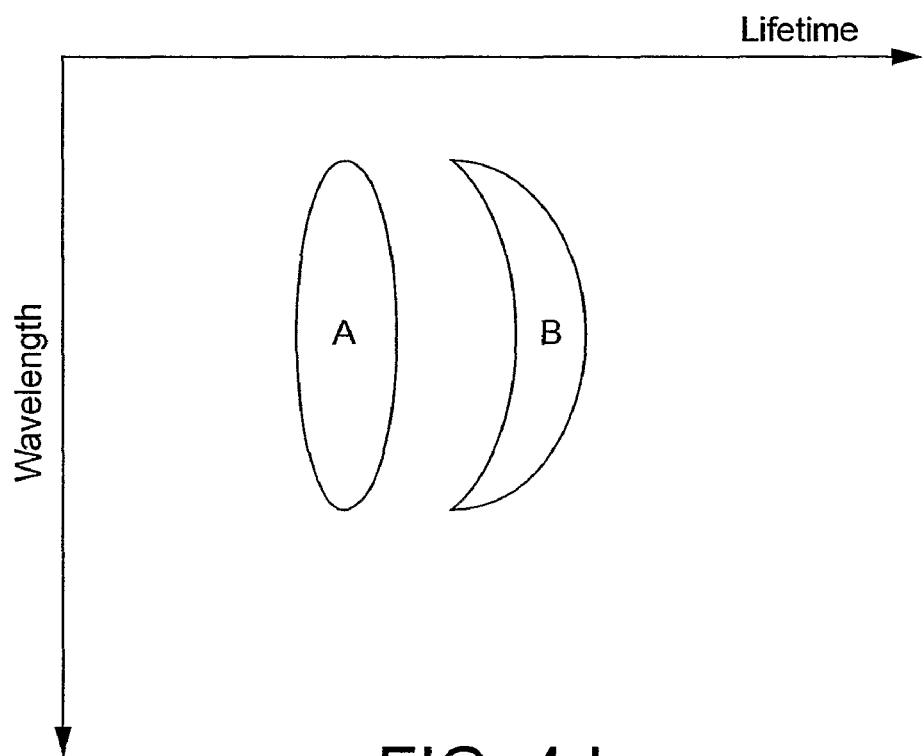
Figure 4E:
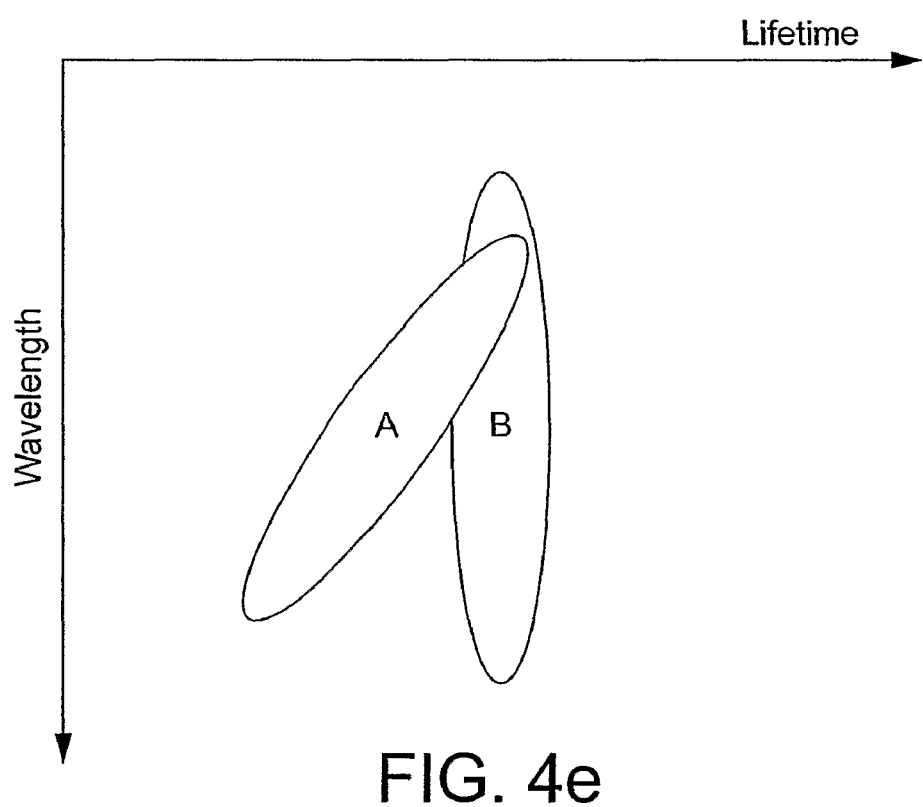
Figure 5:
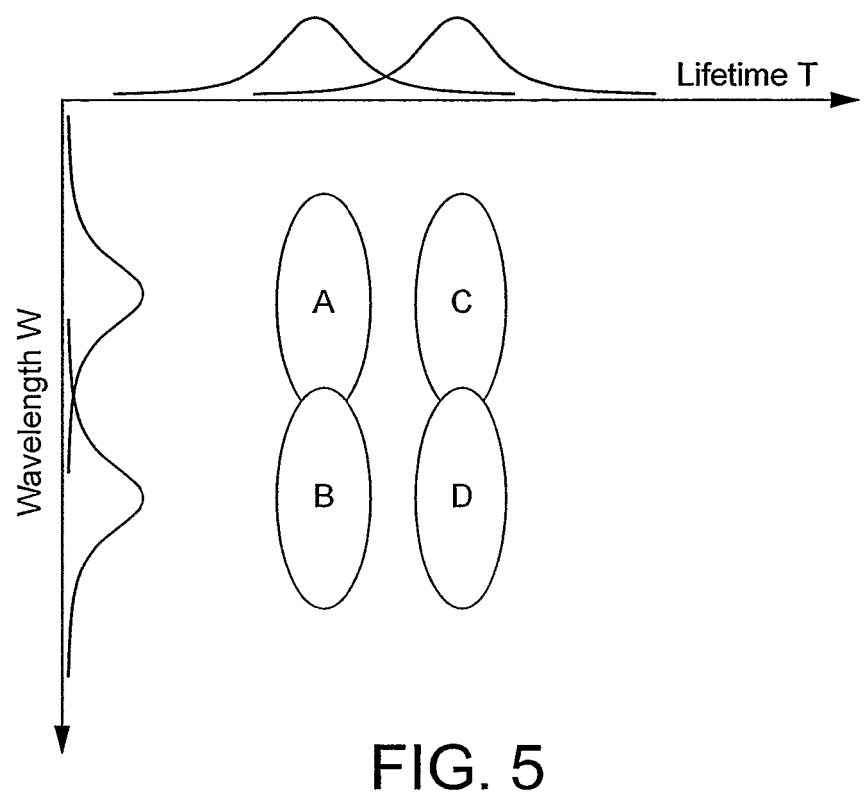
FIG. 5 is a plot of lifetime against wavelength illustrating discrimination between a plurality of fluorescent species according to an embodiment of the invention.
Figure 6:
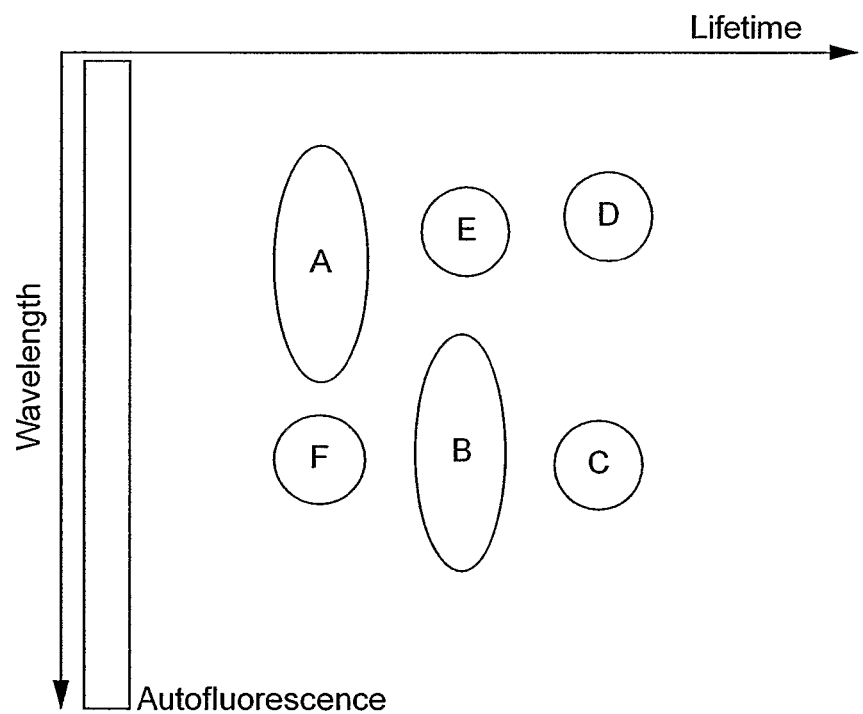
FIG. 6 is a plot of lifetime against wavelength illustrating discrimination between a plurality of fluorescent species according to a further embodiment of the invention.

An embodiment of the invention is presented by way of illustration in FIG. 6, where species A, B, C, D, E and F may be discriminated in the combined wavelength and lifetime domain employing the techniques described herein. A wavelength-only measurement would separate A/E/D from B/C/F but be unable to separate A from E from D, and likewise for B, C and F, while a lifetime-only would separate A/F from B/E from C/D, but again be unable to separate the between these pairs. In fact there is no combination of simple wavelength-only or lifetime-only way of distinguishing these 6 species.

Figure 7:
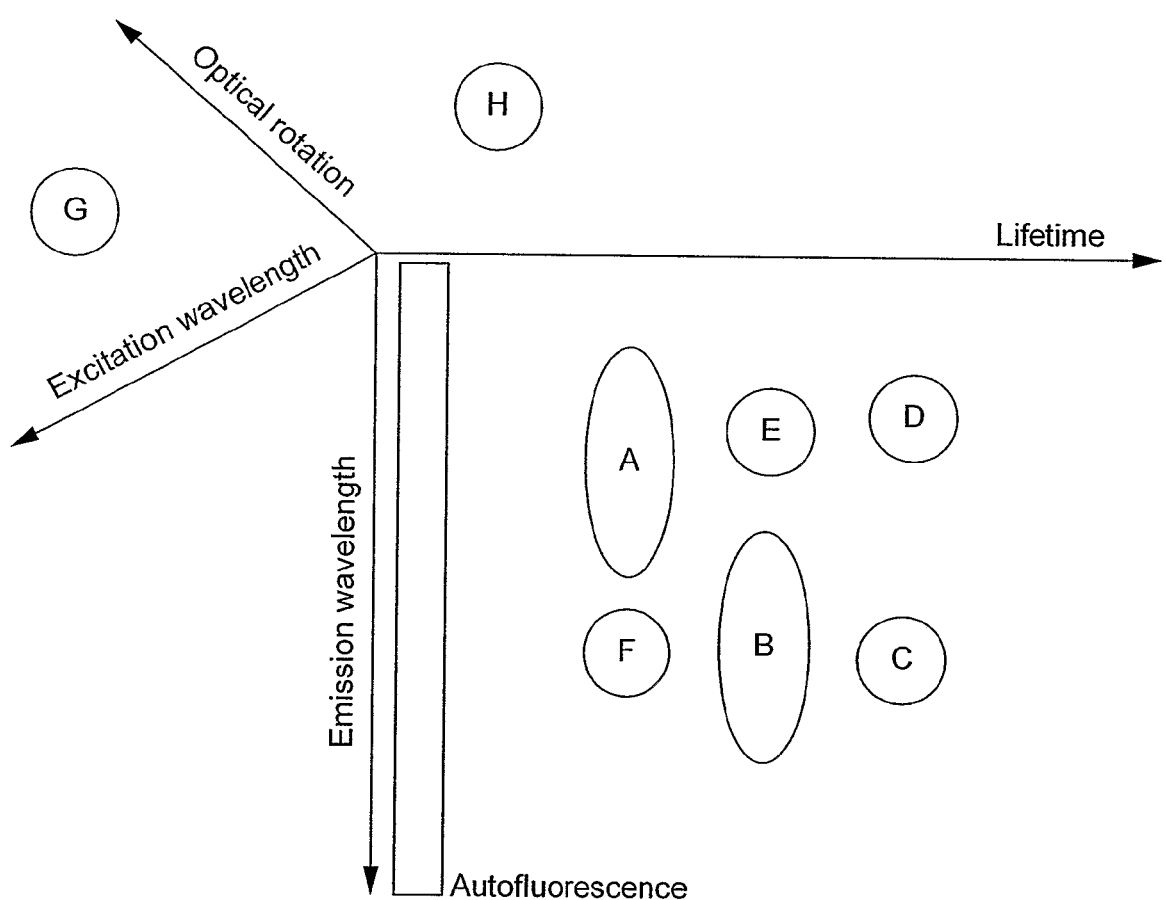
FIG. 7 illustrates discrimination between fluorescent species on a basis of a range of parameters according to a further embodiment of the invention.

The figure clearly shows the large area free to be populated by species allows much greater multiplexing (within limits of detection, time etc). This offers an improved signal to noise due to low background. Interfering auto-fluorescence typically appears in short lifetime region (<2 ns) and may be gated out. The detection can be extended by scanning excitation and/or emission wavelengths and polarisation for estimation of optical rotation (FIG. 7), and combinations thereof.

Figure 8:
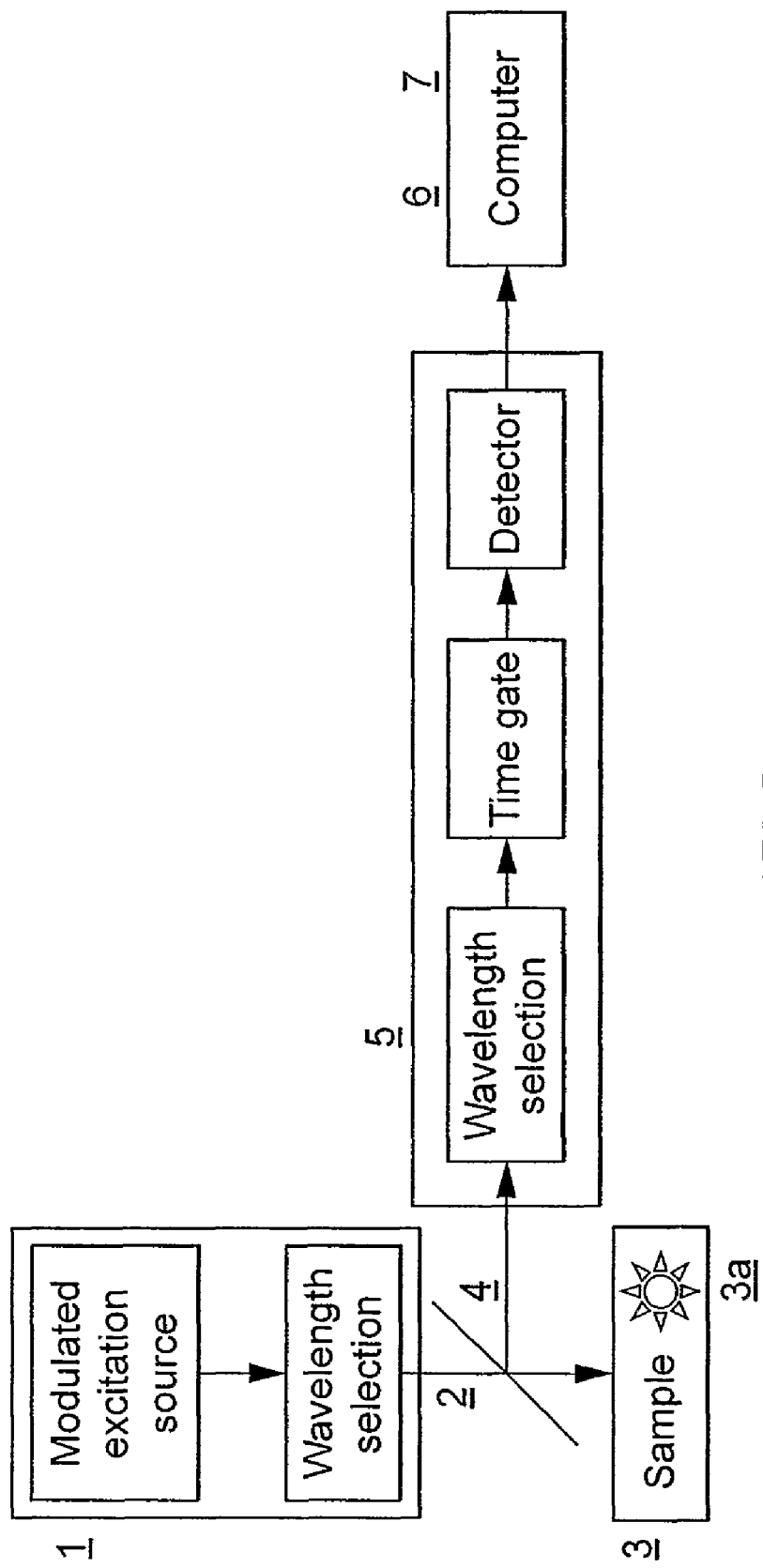
FIG. 8 is a block diagram of a fluorescence detection instrument configuration according to an embodiment of the invention.

An embodiment of apparatus for fluorescence detection is shown in FIG. 8. It comprises:

An excitation light source (1) which may be modulated at least in time and from which an excitation band may be selected;

A delivery means (2) to deliver this excitation energy to a sample;

A sample (3) in a sample holder containing at least one species (3a) with the potential to exhibit at least fluorescence;

A delivery means (4) to deliver emission energy from the sample towards a detector;

One or more detectors (5) onto which emission energy is directed sensitive to some specific aspect of the emission energy including at least time and wavelength using combination of time gating and filters;

A means to capture (6) the signal from the detector/s into a digital storage device such as a computer memory for further processing, analysis and display (7).

In a preferred embodiment, the excitation light source (1) is agile—that is—it may be programmed to emit specific pulse protocols in which the duration of pulses, waveband and power of each pulse, and timing between pulse may be specified and changed quickly. This may be used to selectively excite or saturate particular species in the sample according to the sensitivity of that species to particular pulse types and decay lifetimes, over a wide range, for example combining long ms lifetime lanthanide with short ns lifetime small molecule species thus overcoming dynamic range limitations of existing instruments as well as improving capture speed.

In a further embodiment, the detector (5) is configured to have regions sensitive to different wavebands so that all photons may be captured. Incoming photons are first separated into two beams according to their wavelength band by a dichroic mirror. The photons are then projected onto one of two time-gated detectors. This ensures that every photon within a particular time window is captured by one or other of the detectors. This permits collection of both wavelength and lifetime data and thus more efficient and faster operation with less bleaching.

In another embodiment, the detector (5) is replaced by one which is sensitive to both photon energy and timing [Fraser 2003]. This permits collection of both wavelength and lifetime data and thus more efficient and faster operation with less bleaching.

The excitation light source (1) may comprise one or more lasers, diode laser, DPSS, light emitting diode/s, and/or a supercontinuum source.

The delivery means (2) may comprise one or more lens assemblies, optical fiber, mirror, dichroics, etc.

The sample (3) may comprise a cell, adherent cell layer, suspension of cells, or assembly of beads. The sample holder may include a mechanism for transport along the Z axis, carriage and transport in XY, and incubator for live cells, means for dispensing of fluids, control of temperature. The fluorescent species (3a) may include one or more small fluorescent molecules such as fluorescein, genetically encoded fluorescent molecules such as GFP, intrinsic species such as FAD and NADH, puretime dyes, Eu-chelates, biosensors such as Fura, Quantum dots etc.

The detector (5) may comprise one or more PMTs, a spatially sensitive detector, a gating element such as an MCP, an imaging detector, a spatially partitioned imaging detector, an array of wavelength sensitive detectors, combined with one or more selection mechanisms including time window, waveband and scanning mechanisms for imaging.

The data capture and processing system (6,7) may include means for analysis such as deconvolution and other transforms, and means for collecting a time course series to calculate kinetic data.

Figure 9:
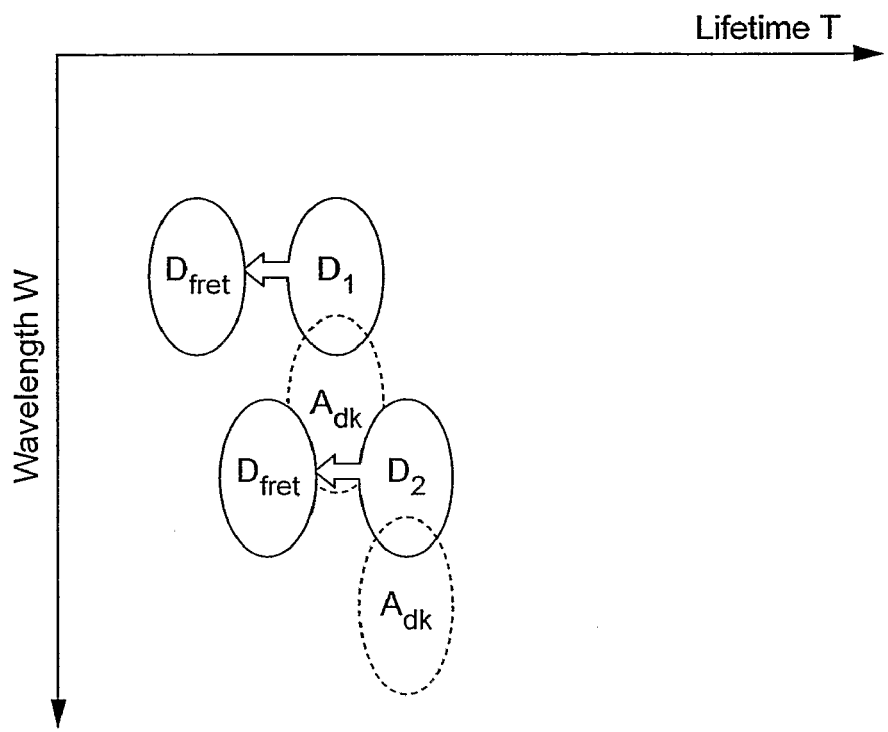
FIG. 9 is a plot of lifetime against wavelength for a FRET application utilising the present invention.

The present method enables robust FRET experiments to be carried out using the FRET-FLIM method and to allow multiple FRET systems to be operated at once to determine for example the sequence of events within a particular cellular pathway. As shown in FIG. 9, one FRET process may be studied by observing the change in lifetime of a donor D1 at a particular waveband, while another FRET process may be studied by observing the change in lifetime of a donor D2 at another waveband.

Figure 10A:
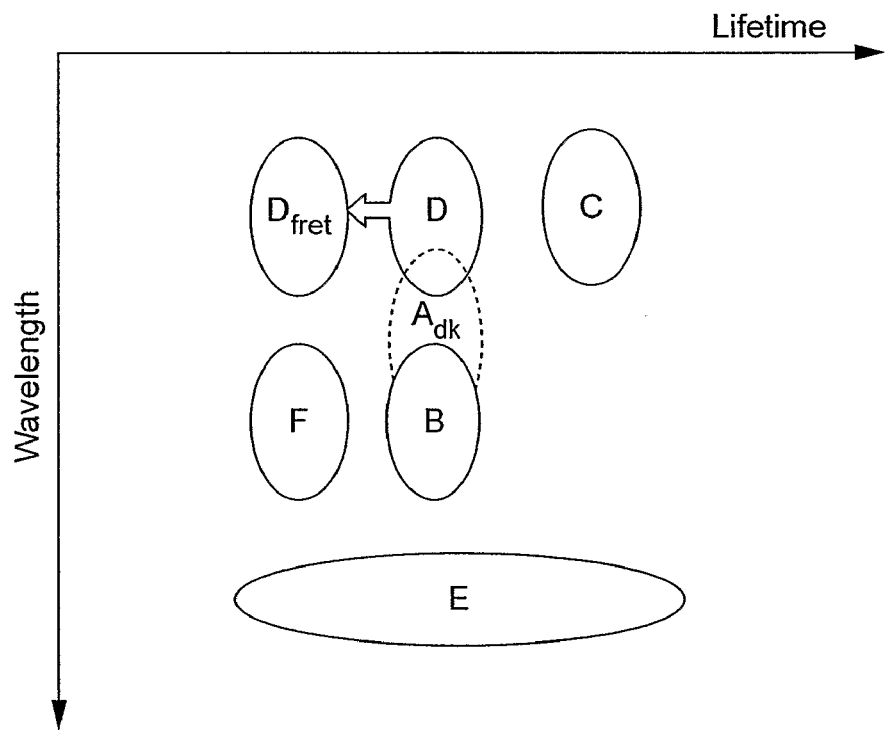
FIGS. 10a to 10c show plots of lifetime against wavelength for three further examples of applications utilising the present invention.
Figure 10B:
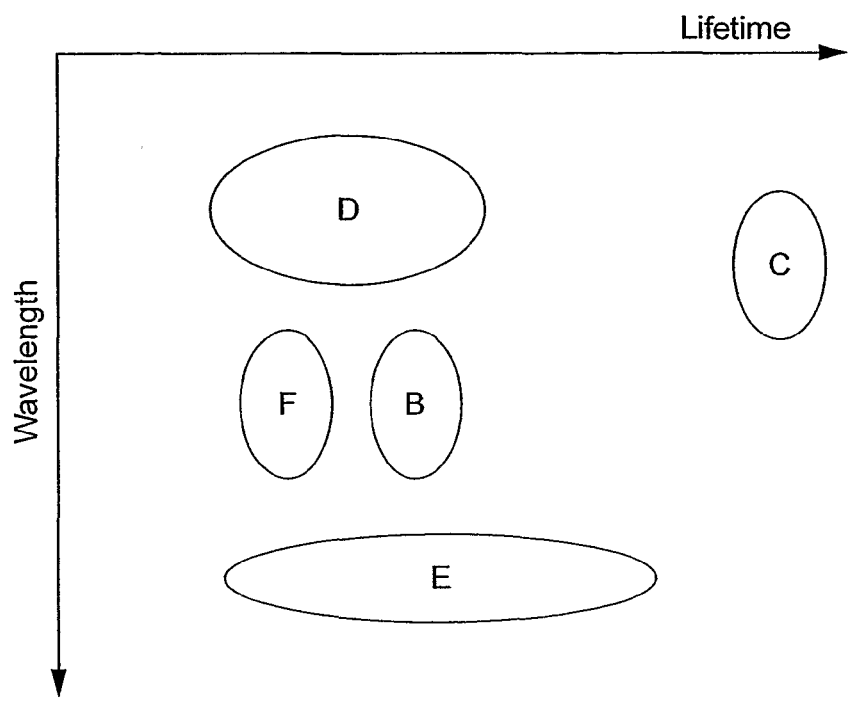
Figure 10C:
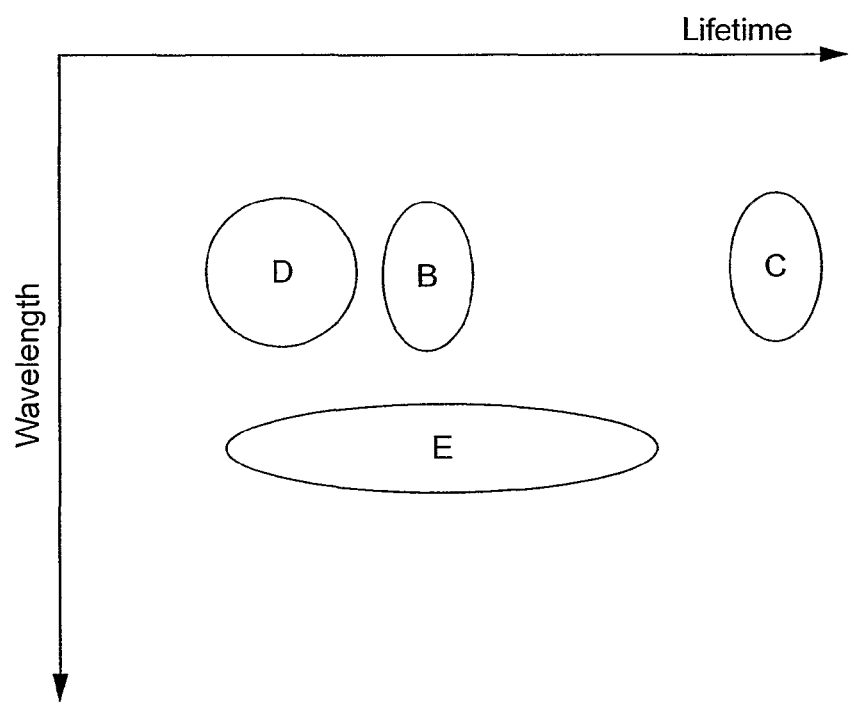

Some further examples of applications utilising the present method are illustrated in FIGS. 10a to 10c. They show the advantage of using combined emission and lifetime to identify and localise characteristics of interest. These examples are only illustrative and it will be appreciated that other combinations are possible with different labels, including intrinsic (naturally present) fluorophores.

Possible characteristics of interest include (1) biological function—for example protein-protein interaction (as indicated by a FRET signal), (2) micro-environment, for example ion concentration such as pH, and (3) presence of a structural or biochemical species, for example DNA or RNA. These three characteristics are often important in drug discovery to understand the state of a live cell as it responds to a stimulus.

FIG. 10a shows the use of a combined emission and lifetime analysis system for an excitation waveband around 488 nm, comprising:
 a functional probe D which represents the donor of a FRET pair e.g. GFP from a GFP-YFP FRET system with emission at 505-530 nm and lifetime between 1.5 ns and 2.5 ns according to the status of the interaction (FRET/no FRET);
 a probe sensing the micro-environment, where B and F represents the extremes of the pH probe Resorufin with emission around 580 nm and a lifetime from 0.5 to 3 ns;
 a structural probe C such as the nuclear stain BODIPY with emission at 500-520 nm with a 6 ns lifetime.

Furthermore, E represents a functionalised quantum dot probe with an emission at 625 nm and a complex lifetime.

FIG. 10b shows another example, also using an excitation waveband around 488 nm, in which D is a nucleic acid probe such as YOYO-1 with emission at 510-550 nm and a lifetime of 1.5 ns when bound to AT-rich DNA and 4.1 ns when bound to GC rich DNA;

C is a functional probe based on the Puretime22 dye with emission at 560 nm with a 22 ns lifetime;

B and F are extremes of an environmental probe such as the lip order dye Di-4-ANEPPDHQ with emission around 570-630 ns and a lifetime from 1.8 to 3.6 ns; and E represents a functionalised quantum dot probe with an emission at 700 nm and a complex lifetime.

The benefit of such a scheme is that several types of qualitative ('is the structure present?') and quantitative ('what is the pH?') question may be asked of the system at the same time, in comparison to conventional approaches which only allow a very small number of qualitative questions.

The examples are for an excitation wavelength of 488 nm or similar. The examples can clearly be extended for other and multiple excitation wavelengths. For example, the excitation band may be switched from 405 nm for a GFP2-YFP FRET pair, to 488 nm for an eGFP-YFP FRET pair.

In a further example (FIG. 10c), an excitation waveband around 360 nm was used, a functional probe B could be used based on a Coumarin derivative with a emission at 450 nm and a lifetime of 3 ns;

the presence of chloride ions could be sensed using a probe C such as MQAE with an emission band at 460 nm and a characteristic lifetime of 25 ns;

a structural component D such as the nucleus could be sensed using the DAPI probe with emission at 460 nm and a lifetime of 0.2-2 ns.

The same system can also simultaneously utilise a series of probes (E) based on functionalised quantum dots which are also excited at 360 nm and each emit in a waveband to be selected according to the quantum dot, typically from 500 nm to 800 nm and beyond.

REFERENCES

R. Neher and E. Neher, Optimizing imaging parameters for the separation of multiple labels in a fluorescence image, J. Microscopy, 213(1), January 2004, pp. 46-62.

S. Vikström, M. Korte, P. Pulli, P. Hurskainen and C. Gripenberg-Lerche, SBS 2004, A Cell-Based, Microplate Format, DELFIA Assay for Determination of the Activation of MAP Kinase.

E. B. van Munster and T. W. J. Gadella, 2005, Fluorescence Lifetime Imaging Microscopy, Advances in Biochem. Eng./Biotechnol. 95, pp 143-175.

C. Schultz, A. Schleifenbaum, J. Goedhart and T. W. Gadella, 2005, Multiparameter imaging for the analysis of intracellular signaling, Chembiochem, August, 6(8), pp. 1323-30.

H. Komatsu, T. Miki, D. Citterio, T. Kubota, Y. Shindo, Y. Kitamura, K. Oka and K. Suzuki, 2005, Single Molecular Multi-analyte ($Ca^{2+}$, $Mg^{2+}$) Fluorescent Probe and Applications to Bioimaging, Am. Chem. Soc., 127 (31), pp. 10798-10799.

S. Vikström, P. Pulli, P. Hurskainen and C. Gripenberg-Lerche, SBS 2004 Orlando Fla., Multiplexing of DELFIA cell proliferation and DNA fragmentation assays with conventional fluorometric cell-based assays for identification of toxic compounds.

Q. S. Hanley, D. J. Arndt-Jovin, T. M. Jovin, 2002, Spectrally resolved fluorescence lifetime imaging microscopy, Applied Spectroscopy, 56, pp. 155-166.

Q. S. Hanley and T. M. Jovin, 2001, Highly Multiplexed Optically Sectioned Spectroscopic Imaging in a Programmable Array Microscope, Appl. Spec., 55 (9), September, pp. 1115-1123.

C. Berney and G. Danuser, 2003, FRET or No FRET: A Quantitative Comparison, Biophysical Journal 84:3992-4010.

G. W. Fraser, J. S. Heslop-Harrison, T. Schwarzacher, A. D. Holland, P. Verhoeve and A. Peacock, 2003, Detection of multiple fluorescent labels using superconducting tunnel junction detectors, Review of Scientific Instruments, September, 74 (9), pp. 4140-4144.

S. Ganesan, S. M. Ameer-beg, T. T. C. Ng, B. Vojnovic and F. S. Wouters, 6 Mar. 2006, A dark yellow fluorescent protein (YFP)-based Resonance Energy-Accepting Chromoprotein (REACh) for Förster resonance energy transfer with GFP, PNAS, March 14, vol. 103(11) pp. 4089-4094.

ISS website http://www.iss.com/resources/fluorophores.html; http://www.assaymetrics.com

The invention claimed is:

1. A method of analysing a biological sample comprising:
   (a) providing a biological sample including a plurality of fluorescent species;
   (b) irradiating the sample with a pulse of excitation energy causing fluorescent species in the sample to fluoresce;
   (c) detecting light emanating from the sample during a predetermined period of time after the pulse;
   (d) generating and storing data recording at least the wavelength of the detected light against time; and
   (e) analysing the data with reference to the respective lifetimes of the fluorescent species to detect the presence of and discriminate between the respective emissions from three or more different fluorescent species which emit light simultaneously during at least part of said predetermined period, which are indistinguishable from each other on the basis of their wavelength or lifetime alone.

2. A method of claim 1 wherein the detection step (c) comprises detecting the intensity distribution of the light emanating from the sample across a range of wavelengths over said predetermined period of time, and detecting the combined intensity of the light emanating from the sample over said predetermined period of time.

3. A method of claim 1 wherein the sample is irradiated by scanning a range of excitation energies.

4. A method of claim 1 wherein the sample is irradiated in step (b) by a plurality of pulses of excitation energy.

5. A method of claim 1 wherein data related to the polarisation of light emanating from the sample is stored in step (d) and employed in analysis step (e).

6. A method of claim 1 wherein the spatial distribution of the light emanating from the sample is detected and recorded.

7. A method of claim 1 wherein light is detected at a predetermined series of intervals during the predetermined period of time.

8. Apparatus for analysing a biological sample including a plurality of fluorescent species, the apparatus including processing means for analysing data recording against time at least the wavelength of light emanating from a sample during a predetermined period of time, with reference to the respective lifetimes of the fluorescent species, to detect the presence of and discriminate between the respective emissions from three or more different fluorescent species which emit light simultaneously during at least part of said predetermined period, which emissions are otherwise indistinguishable from each other on the basis of their wavelength or lifetime alone.

9. Apparatus of claim 8 including light detection means selected from the following: at least one PMT, a spatially sensitive detector, an imaging detector, a spatially partitioned imaging detector, and an array of wavelength sensitive detectors.

* * * * *